United States Patent [19]

Syoshi et al.

[11] Patent Number: 5,241,102
[45] Date of Patent: Aug. 31, 1993

[54] SCHIFF BASE COMPOUNDS

[75] Inventors: Masayuki Syoshi; Miwa Syutou, both of Yokohama, Japan

[73] Assignee: Ricoh Company, Ltd., Tokyo, Japan

[21] Appl. No.: 859,608

[22] Filed: Mar. 20, 1992

Related U.S. Application Data

[63] Continuation of Ser. No. 528,742, May 24, 1990, abandoned.

[30] Foreign Application Priority Data

| | | | |
|---|---|---|---|
| May 29, 1989 | [JP] | Japan | 1-135544 |
| May 29, 1989 | [JP] | Japan | 1-135545 |
| May 29, 1989 | [JP] | Japan | 1-135546 |
| Feb. 14, 1990 | [JP] | Japan | 2-33531 |

[51] Int. Cl.$^5$ .............. C07C 229/00; C07C 233/00; C07C 235/00; C07C 237/00
[52] U.S. Cl. .............................. 560/35; 560/21; 564/163; 564/166; 564/167
[58] Field of Search ............ 560/21, 35; 564/163, 564/163.6, 167

[56] References Cited

U.S. PATENT DOCUMENTS 4,576,732 3/1986 Isogai et al. ................ 252/299.65

OTHER PUBLICATIONS

Chemical Abstracts 115(9), 91, 849 Shoji et al. Jpn. Kokai Tokkyo Koho JP03 86,854 Apr. 11, 1991.

*Primary Examiner*—Mukund J. Shah
*Assistant Examiner*—Matthew V. Grumbling
*Attorney, Agent, or Firm*—Cooper & Dunham

[57] ABSTRACT

A Schiff base compound of formula (I):

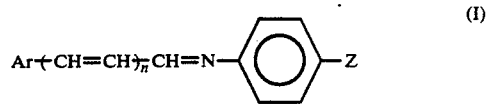

(I)

wherein Ar represents an aromatic group, which may have a substituent; n is 0 or 1; and Z represents

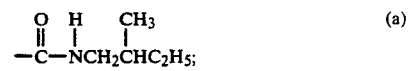
(a)

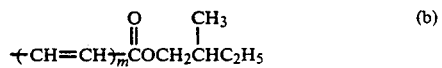

(b)

in which m is an integer of 0 or 1, or

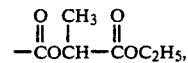

provided that when Z is

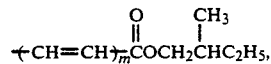

and Ar is a phenyl group and the substituent thereof is an alkoxyl group represented by $C_pH_{2p+1}O$, p is an integer of 1 to 4.

In addition, a nonlinear optical material using the above Schiff base compound of formula (I) is disclosed.

2 Claims, 6 Drawing Sheets

SCHIFF BASE COMPOUNDS

The is a continuation of application Ser. No. 528,742, filed May 24, 1990, now abandoned.

BACKGROUND OF THE INVENTION

1. Field of the Invention

The present invention relates to Schiff base compounds and nonlinear optical materials comprising the Schiff base compounds, which are applicable to electro-optical devices, such as a second higher harmonic generation device, a piezoelectric device, an optical waveguide, a light source for an optical memory and a laser printer, and an optical switching device.

2. Discussion of the Background

In recent years, much attention is focused on materials having a nonlinear optical effect. When a laser beam having a relatively strong light intensity is applied to such materials, a light beam with a different light component from that of the applied laser beam is emitted therefrom. Such materials are conventionally known as nonlinear optical materials and described, for instance, in the following references: "Nonlinear Optical Properties of Organic and Polymeric Materials" ACS SYMPOSIUM SERIES 233, edited by David J. Williams (American Chemical Society, 1983), "Organic Nonlinear Optical Materials" compiled by Masao Kato and Hachiro Nakanishi (CMC Co., Ltd., 1983), and "Organic Electronics Materials" edited by Akio Taniguchi (Science Forum Co., Ltd., 1986).

The nonlinear optical materials are used in practice, for example, in a second higher harmonic generation (SHG) device, which utilizes a secondary nonlinear optical effect of the materials, and in a wavelength conversion device. Specific examples of the nonlinear optical materials which are employed in practice in the above devices are inorganic compounds such as potassium dihydrogenphosphate (KDP), ammonium dihydrogenphosphate (ADP) and lithium niobate. Recently it has been discovered that $\pi$-electron-conjugated organic compounds having electron donative groups and electron attractive groups surpass the above-mentioned inorganic compounds in the nonlinear optical effect.

Generally, in the case of organic compounds, each molecule shows a nonlinear optical response and the nonlinear optical performance of each molecule depends upon the magnitude of the molecular hyperpolarizability ($\beta$). However, many organic compounds, as represented by p-nitroaniline, have high second nonlinear optical performance, that is, high molecular hyperpolarizability ($\beta$), in a gas state in which each molecule is separately and independently present, but never show the second nonlinear optical properties in a crystalline state, because in the crystalline state, such compounds have a centrosymmetric structure in the molecular arrangement thereof and therefore no molecular hyperpolarizability is exhibited.

As described in J. Appl. Phys. 50,2523 (1970) by B. F. Levine, et al., 2-methyl-4-nitroaniline (MNA), which is prepared by introducing a methyl group at an orthoposition of the above-mentioned p-nitroaniline, does not have such a centrosymmetrical structure as in p-nitroaniline since the centrosymmetrical structure is successfully destroyed by the introduction of a methyl group, but maintains the same high molecular hyperpolarizability ($\beta$) as in p-nitroaniline, so that the thus obtained MNA has a large second higher harmonic generation tensor $d_{11}$. However, the MNA does not satisfy the conditions under which second higher harmonic generation can be effectively obtained. Therefore, it is extremely difficult to effectively utilize the large nonlinear optical performance of the MNA.

In addition, it is extremely difficult to obtain the MNA in a single crystalline state, so that this compound is is not suitable for the material for use in nonlinear optical devices.

Furthermore, a method of obtaining a nonlinear optical medium by dispersing a compound with high nonlinear optical effect in a ploymeric material and subjecting the dispersion to poling under application of a magnetic field is disclosed in Japanese Laid-Open Patent Application 61-186942. However this method does not necessarily provide a satisfactory optical medium.

SUMMARY OF THE INVENTION

Accordingly, a first object of the present invention is to provide compounds having an excellent nonlinear optical effect.

A second object of the present invention is to provide starting materials for preparing the above-mentioned compounds.

A third object of the present invention is to provide improved nonlinear optical materials comprising the above-mentioned compounds.

The first object of the present invention can be achieved by Schiff base compounds represented by the following formula (I):

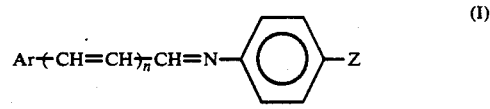

wherein Ar represents an aromatic group, which may have a substituent; n is 0 or 1; and Z represents

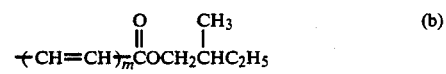

in which m is an integer of 0 or 1, or

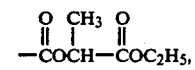

provided that when Z is

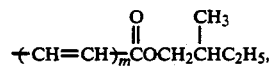

and Ar is a phenyl group and the substituent thereof is an alkoxyl group represented by $C_pH_{2p+1}O$, p is an integer of 1 to 4.

The second object of the present invention can be achieved by p-aminobenzoic acid (N'-2-methylbutyl)amide having formula (A), and p-aminobenzoic acid (1-ethoxycarbonylethyl)ester having formula (B):

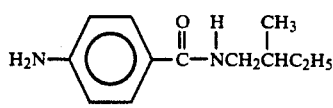
(A)

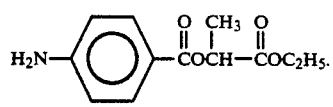
(B)

The third object of the present invention can be achieved by nonlinear optical materials comprising the above-mentioned Schiff base compounds of formula (I).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
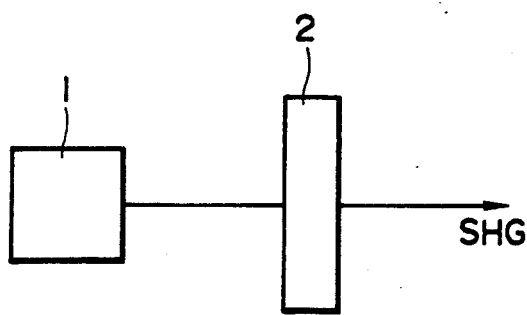
FIG. 1 is a schematic diagram showing an example of the second higher harmonic generation device using a nonlinear optical material according to the present invention.

The Schiff base compounds according to the present invention are represented by the following formula:

(I)

wherein Ar represents an aromatic group, which may have a substituent; n is 0 or 1; and Z represents

(a)

in which m is an integer of 0 or 1, or

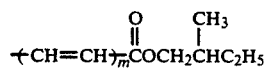
(b)

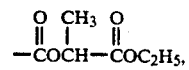

provided that when Z is

and Ar is a phenyl group and the substituent thereof is an alkoxyl group represented by $C_pH_{2p+1}O$, p is an integer of 1 to 4.

Examples of the aromatic group represented by Ar in formula (I) are a phenyl group; a polycyclic aromatic group such as a naphthalene group, an anthracene group and a pyrene group; and an aromatic heterocyclic group such as a carbazole group, an indole group, a phenothiazine group, a furan group and a thiophene group. These aromatic groups may have a substituent.

Examples of the substituent of the aromatic group represented by Ar in formula (I) are an amino group having as a substituent at least one alkyl group having 1 to 4 carbon atoms, a phenyl group or a benzyl group; a hydroxyl group; an alkoxyl group having 1 to 16 carbon atoms, which may have a phenyl group as a substituent; a phenyl group which may have as a substituent an alkyl group having 1 to 6 carbon atoms or an alkoxyl group having 1 to 16 carbon atoms; an alkyl group having 1 to 10 carbon atoms, which may have a phenyl group as a substituent; a halogen such as chlorine or bromine; an alkoxycarbonyl group having formula of $—COOC_lH_{2l+1}$ in which l is 1 to 16; a cyano group; and a nitro group.

The above-mentioned Schiff base compounds according to the present invention can be prepared by allowing an aldehyde compound having formula (II) to react with a compound selected from the group consisting of p-aminobenzoic acid (N'-2-methylbutyl)amide of formula (III-1), an aniline derivative having formula (III-2) or p-aminobenzoic acid (1-ethoxy-carbonylethyl)ester of formula (III-3):

(II)

wherein Ar is the same as previously defined in formula (1); and n is 0 or 1.

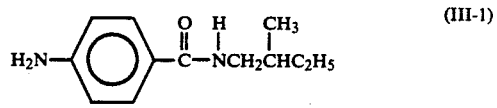
(III-1)

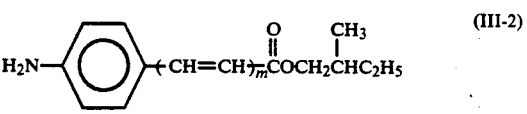
(III-2)

wherein m is an integer of 0 or 1,

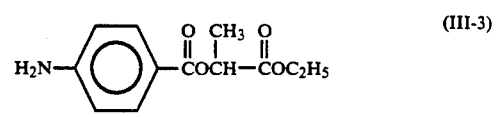
(III-3)

This reaction is generally carried out by subjecting a mixture of the above-mentioned aldehyde compound and the compound of formula (III-1), (III-2) or (III-3) to condensation reaction in a non-aqueous solvent at room temperature. Examples of the solvent used in the condensation reaction are absolute alcohol, ethyl acetate and toluene.

In the course of the condensation reaction, acids such as acetic acid and p-toluenesulfonic acid can be used as catalysts when necessary.

The amount ratio of the aldehyde compound having formula (II) to the compound having formula (III-1), (III-2) or (III-3) may be stoichiometric.

The compound of formula (III-1), p-aminobenzoic acid (N'-2-methylbutyl)amide, can be prepared in the following reaction scheme in which 4-nitrobenzoic acid chloride of formula (IV-1) is allowed to react with 2-methyl-1-butylamine of formula (V-1) in the presence of a basic catalyst such as pyridine, so that p-nitrobenzoic acid (N-2-methylbutyl)amide of formula (VI-1) is obtained, and the thus obtained p-nitrobenzoic acid (N-2-methylbutyl)amide is then reduced in the presence of a reduction catalyst such as Pd-C:

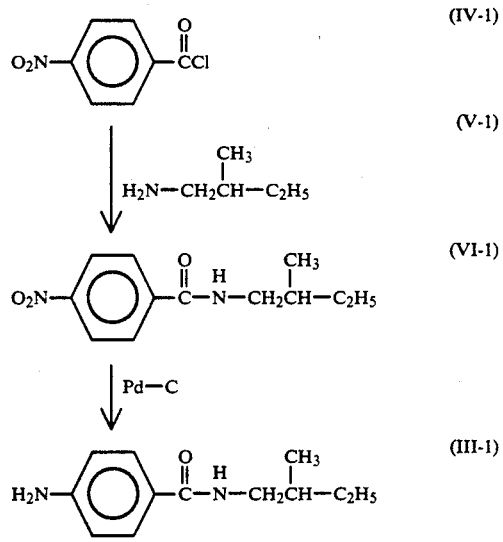

In the above reaction scheme, when the 2-methyl-1-butylamine of formula (V-1) is replaced by optical active 2-methyl-1-butylamine, the corresponding optical active p-aminobenzoic acid (N'-2-methylbutyl)amide can be prepared.

The compound of formula (III-2) is conventionally known and can be prepared by the following reaction scheme, in which, for example, 4-nitrobenzoic acid chloride (the compound with m=0 in formula (IV-2)) or 4-nitrocinnamic acid chloride (the compound with m=1 in formula (IV-2)) is allowed to react with 2-methyl-1-butanol of formula (V-2) in the presence of a basic catalyst such as pyridine, so that 4-nitrobenzoic acid-2-methylbutyl ester (the compound with m=0 in formula (VI-2)) or 4-nitrocinnamic acid-2-methylbutyl ester (the compound with m=1 in formula (VI-2) is obtained, and the thus obtained 4-nitrobenzoic acid-2-methylbutyl ester or 4-nitrocinnamic acid-2-methylbutyl ester is reduced:

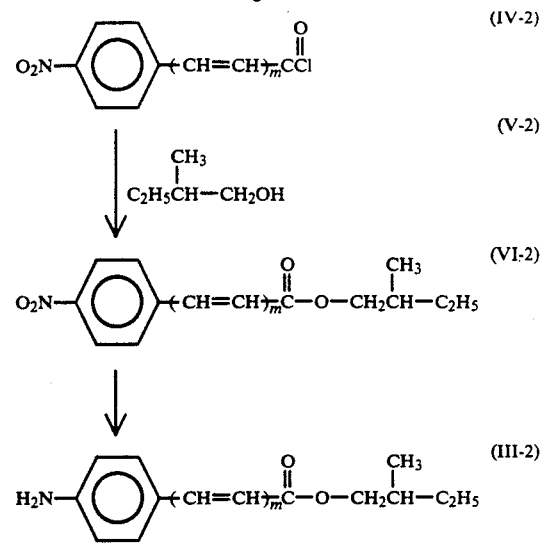

In the above reaction scheme, when the 2-methyl-1-butanol of formula (V-2) is replaced by optical active 2-methyl-1-butanol, the corresponding optical active aniline of formula (III-2) can be prepared.

The compound of formula (III-3), p-aminobenzoic acid-(1-ethoxycarbonylethyl)ester, can be prepared by the following reaction scheme in which 4-nitrobenzoic acid chloride of formula (IV-3) is allowed to react with ethyl lactate of formula (V-3) in the presence of a basic catalyst such as pyridine, so that p-nitrobenzoic acid (1-ethoxycarbonylethyl)ester of formula (VI-3) is obtained, and the thus obtained p-nitrobenzoic acid (1-ethoxycarbonylethyl)ester is reduced in the presence of a reduction catalyst such as Pd-C:

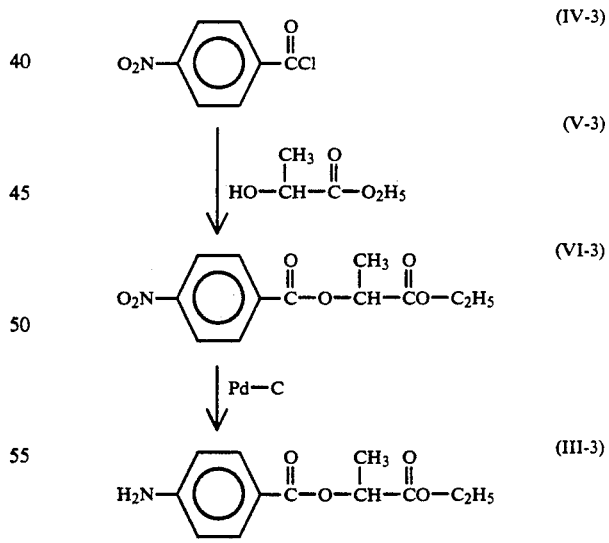

In the above reaction scheme, when the ethyl lactate of formula (V-3) is replaced by optical active ethyl lactate, the corresponding optical active p-aminobenzoic acid (1-ethoxycarbonylethyl)ester of formula (III-3) can be prepared.

Specific examples of the Schiff base compounds of formula (I) according to the present invention are listed in the following Tables.

The Schiff base compounds which are prepared by using the p-aminobenzoic acid (N'-2-methylbutyl)amide having formula (III-1) are represented by formula (I-1), and specific examples thereof are listed in Table 1.

The Schiff base compounds which are prepared by using the anilines having formula (III-2) are represented by formula (I-2), and specific examples thereof are listed in Table 2.

The Schiff base compounds which are prepared by using the p-aminobenzoic acid(1-ethoxycarbonylethyl)ester having formula (III-3) are represented by formula (I-3), and specific examples thereof are listed in Table 3.

TABLE 1

[Schiff base compounds having formula (I-1) prepared by use of p-aminobenzoic acid(N'-2-methylbutyl)amide of formula (III-1)]

$$Ar(CH=CH)_n CH=N-\underset{}{\underset{}{\bigcirc}}-\underset{O}{\overset{}{C}}-\underset{H}{\overset{}{N}}-CH_2\underset{CH_3}{\overset{}{C}H}C_2H_5$$

(I-1)

| Schiff Base Compound No. | n | Ar |
|---|---|---|
| 1 - 1 | 0 | 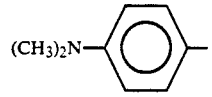 |
| 1 - 2 | 0 | 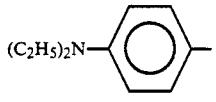 |
| 1 - 3 | 0 | 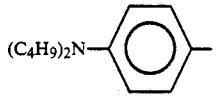 |
| 1 - 4 | 1 | 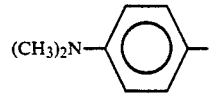 |
| 1 - 5 | 0 | 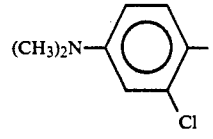 |
| 1 - 6 | 0 | 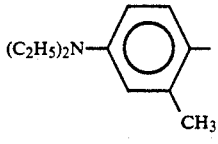 |
| 1 - 7 | 0 | 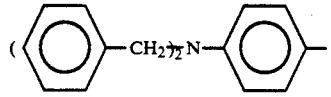 |
| 1 - 8 | 0 | 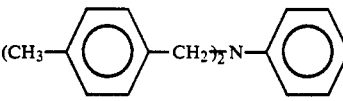 |
| 1 - 9 | 0 | 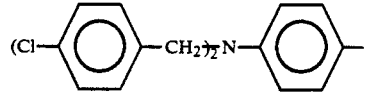 |
| 1 - 10 | 0 | 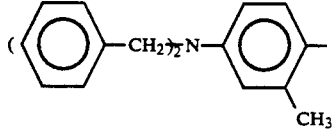 |
| 1 - 11 | 0 | 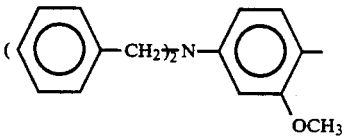 |
| 1 - 12 | 0 | 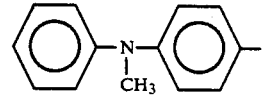 |
| 1 - 13 | 0 | 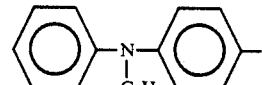 |
| 1 - 14 | 0 | 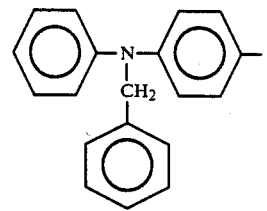 |
| 1 - 15 | 0 | 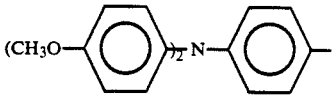 |
| 1 - 16 | 0 | 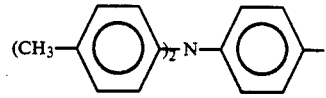 |
| 1 - 17 | 0 | 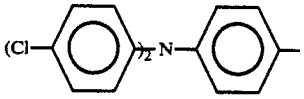 |
| 1 - 18 | 0 | 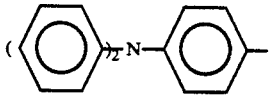 |
| 1 - 19 | 0 | 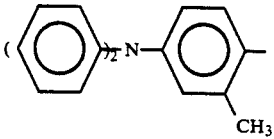 |

TABLE 1-continued
| | | |
|---|---|---|
| 1 - 20 | 0 | 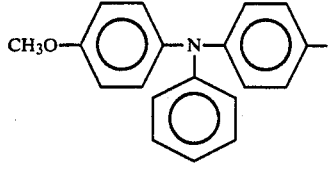 |
| 1 - 21 | 0 | 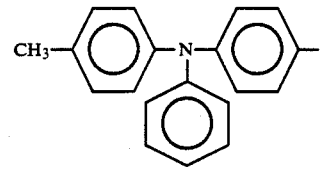 |
| 1 - 22 | 0 | 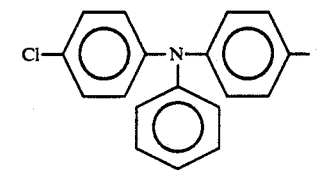 |
| 1 - 23 | 0 | 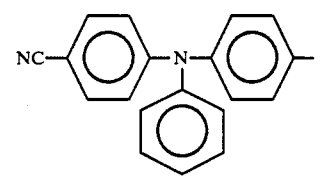 |
| 1 - 24 | 0 | 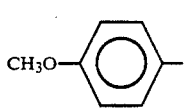 |
| 1 - 25 | 0 | 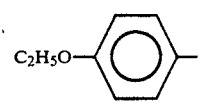 |
| 1 - 26 | 0 | 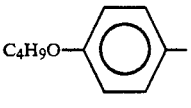 |
| 1 - 27 | 0 | 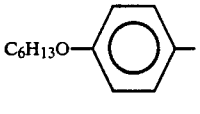 |
| 1 - 28 | 0 | 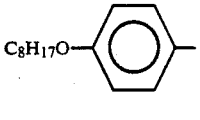 |
| 1 - 29 | 0 | 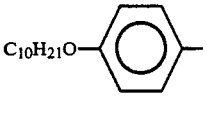 |
| 1 - 30 | 0 | 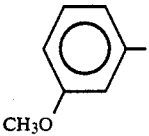 |
| 1 - 31 | 0 | 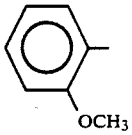 |
| 1 - 32 | 0 | 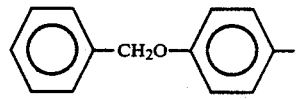 |
| 1 - 33 | 1 | 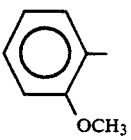 |
| 1 - 34 | 0 | 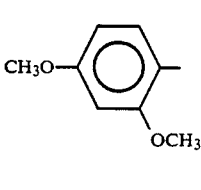 |
| 1 - 35 | 0 | 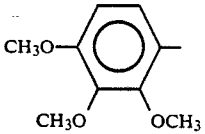 |
| 1 - 36 | 0 | 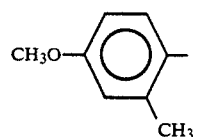 |
| 1 - 37 | 0 | 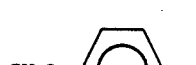 |
| 1 - 38 | 0 | 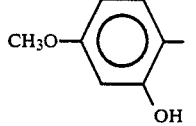 |
| 1 - 39 | 0 | 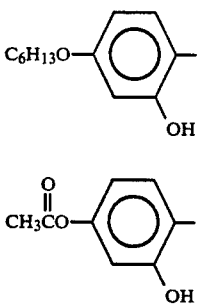 |
| 1 - 40 | 0 | 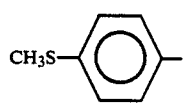 |
| 1 - 41 | 0 | 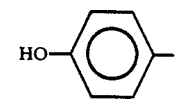 |

TABLE 1-continued
| | | |
|---|---|---|
| 1 - 42 | 0 | 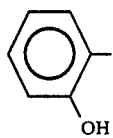 |
| 1 - 43 | 0 | 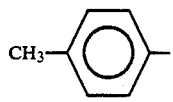 |
| 1 - 44 | 0 | 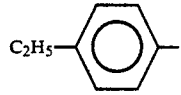 |
| 1 - 45 | 0 | 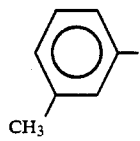 |
| 1 - 46 | 0 | 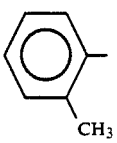 |
| 1 - 47 | 0 | 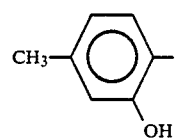 |
| 1 - 48 | 0 | 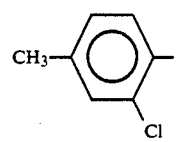 |
| 1 - 49 | 0 | 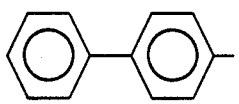 |
| 1 - 50 | 0 | 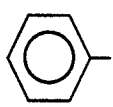 |
| 1 - 51 | 1 | 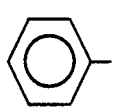 |
| 1 - 52 | | 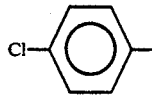 |
| 1 - 53 | 0 | 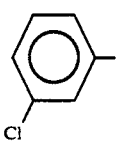 |
TABLE 1-continued
| | | |
|---|---|---|
| 1 - 54 | 0 | 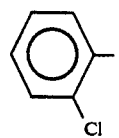 |
| 1 - 55 | 0 | 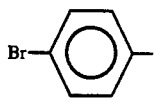 |
| 1 - 56 | 0 | 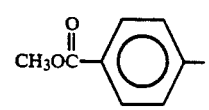 |
| 1 - 57 | 0 | 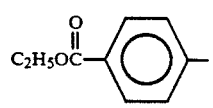 |
| 1 - 58 | 0 | 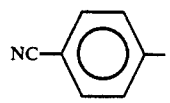 |
| 1 - 59 | 0 | 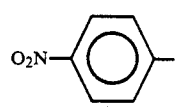 |
| 1 - 60 | 0 | 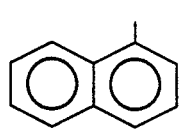 |
| 1 - 61 | 0 | 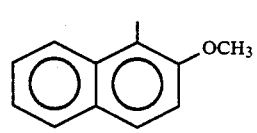 |
| 1 - 62 | 0 | 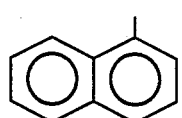 |
| 1 - 63 | 0 | 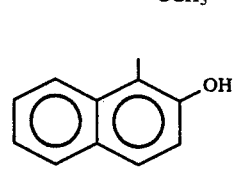 |
| 1 - 64 | 0 | 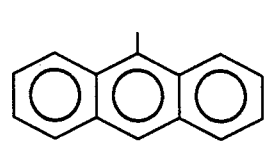 |

TABLE 1-continued

| No. | n | Structure |
|---|---|---|
| 1-65 | 0 | (pyrene with methyl) |
| 1-66 | 0 | (N-methyl carbazole) |
| 1-67 | 0 | (N-ethyl carbazole) |
| 1-68 | 0 | (N-butyl carbazole) |
| 1-69 | 0 | (indole, NH) |
| 1-70 | 0 | (phenothiazine, NH) |
| 1-71 | 0 | (phenothiazine, N-COCH₃) — N—O=C—CH₃ |
| 1-72 | 0 | (phenothiazine, N-CH₃) |
| 1-73 | 0 | (furan with methyl) |
| 1-74 | 0 | (thiophene with methyl) |

TABLE 2

[Schiff base compounds having formula (I-2) prepared by use of anilines of formula (III-2)]

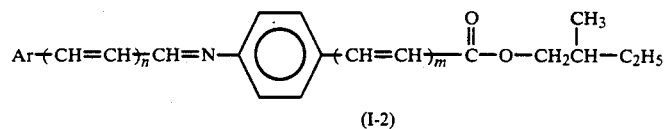

$$Ar\text{-}(CH=CH)_n\text{-}CH=N\text{-}\underset{}{\bigcirc}\text{-}(CH=CH)_m\text{-}\overset{O}{\underset{\|}{C}}\text{-}O\text{-}CH_2\overset{CH_3}{\underset{|}{CH}}\text{-}C_2H_5$$

(I-2)

| Schiff Base Compound No. | n | m | Ar |
|---|---|---|---|
| 2-1 | 0 | 0 | (CH₃)₂N—⟨phenyl⟩— |
| 2-2 | 1 | 0 | (CH₃)₂N—⟨phenyl⟩— |
| 2-3 | 0 | 1 | (CH₃)₂N—⟨phenyl⟩— |
| 2-4 | 1 | 1 | (CH₃)₂N—⟨phenyl⟩— |

TABLE 2-continued

[Schiff base compounds having formula (I-2)
prepared by use of anilines of formula (III-2)]

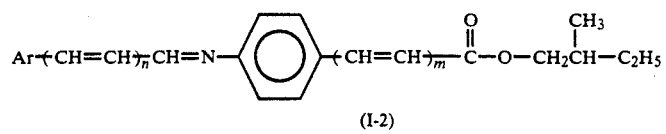

(I-2)

| Schiff Base Compound No. | n | m | Ar |
|---|---|---|---|
| 2 - 5 | 0 | 0 | (C$_2$H$_5$)$_2$N—⟨C$_6$H$_4$⟩— |
| 2 - 6 | 0 | 1 | (C$_2$H$_5$)$_2$N—⟨C$_6$H$_4$⟩— |
| 2 - 7 | 0 | 1 | (C$_4$H$_9$)$_2$N—⟨C$_6$H$_4$⟩— |
| 2 - 8 | 0 | 0 | (CH$_3$)$_2$N—⟨C$_6$H$_3$(CH$_3$)⟩— |
| 2 - 9 | 0 | 1 | (CH$_3$)$_2$N—⟨C$_6$H$_3$(CH$_3$)⟩— |
| 2 - 10 | 0 | 0 | (C$_2$H$_5$)$_2$N—⟨C$_6$H$_3$(Cl)⟩— |
| 2 - 11 | 0 | 1 | (C$_2$H$_5$)$_2$N—⟨C$_6$H$_3$(Cl)⟩— |
| 2 - 12 | 0 | 0 | (C$_6$H$_5$—CH$_2$)$_2$N—⟨C$_6$H$_4$⟩— |
| 2 - 13 | 0 | 1 | (C$_6$H$_5$—CH$_2$)$_2$N—⟨C$_6$H$_4$⟩— |
| 2 - 14 | 0 | 0 | (CH$_3$—C$_6$H$_4$—CH$_2$)$_2$N—⟨C$_6$H$_4$⟩— |

TABLE 2-continued

[Schiff base compounds having formula (I-2) prepared by use of anilines of formula (III-2)]

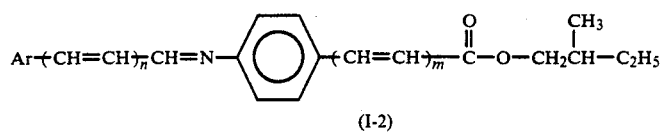

(I-2)

| Schiff Base Compound No. | n | m | Ar |
|---|---|---|---|
| 2 - 15 | 0 | 1 | (Cl—⟨phenyl⟩—CH$_2$)$_2$N—⟨phenyl⟩— |
| 2 - 16 | 0 | 1 | (⟨phenyl⟩—CH$_2$)$_2$N—⟨phenyl with CH$_3$⟩— |
| 2 - 17 | 0 | 0 | (⟨phenyl⟩—CH$_2$)$_2$N—⟨phenyl with OCH$_3$⟩— |
| 2 - 18 | 0 | 0 | ⟨phenyl⟩—N(CH$_3$)—⟨phenyl⟩— |
| 2 - 19 | 0 | 1 | ⟨phenyl⟩—N(C$_2$H$_5$)—⟨phenyl⟩— |
| 2 - 20 | 0 | 0 | ⟨phenyl⟩—N(CH$_2$-phenyl)—⟨phenyl⟩— |
| 2 - 21 | 0 | 1 | ⟨phenyl⟩—N(CH$_2$-phenyl)—⟨phenyl⟩— |
| 2 - 22 | 0 | 1 | (CH$_3$O—⟨phenyl⟩—)$_2$N—⟨phenyl⟩— |
| 2 - 23 | 0 | 1 | (CH$_3$—⟨phenyl⟩—)$_2$N—⟨phenyl⟩— |

TABLE 2-continued
[Schiff base compounds having formula (I-2) prepared by use of anilines of formula (III-2)]
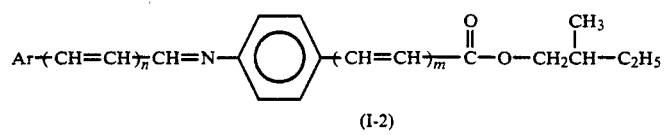
(I-2)
| Schiff Base Compound No. | n | m | Ar |
|---|---|---|---|
| 2 - 24 | 0 | 1 | (Cl—⟨C₆H₄⟩)₂N—⟨C₆H₄⟩— |
| 2 - 25 | 0 | 0 | (⟨C₆H₅⟩)₂N—⟨C₆H₄⟩— |
| 2 - 26 | 0 | 1 | (⟨C₆H₅⟩)₂N—⟨C₆H₄⟩— |
| 2 - 27 | 0 | 1 | CH₃O—⟨C₆H₄⟩—N(⟨C₆H₅⟩)—⟨C₆H₄⟩— |
| 2 - 28 | 0 | 0 | CH₃—⟨C₆H₄⟩—N(⟨C₆H₅⟩)—⟨C₆H₄⟩— |
| 2 - 29 | 0 | 1 | Cl—⟨C₆H₄⟩—N(⟨C₆H₅⟩)—⟨C₆H₄⟩— |
| 2 - 30 | 0 | 0 | NC—⟨C₆H₄⟩—N(⟨C₆H₅⟩)—⟨C₆H₄⟩— |
| 2 - 31 | 0 | 0 | (⟨C₆H₅⟩)₂N—⟨C₆H₃(CH₃)⟩— |

TABLE 2-continued
[Schiff base compounds having formula (I-2)
prepared by use of anilines of formula (III-2)]
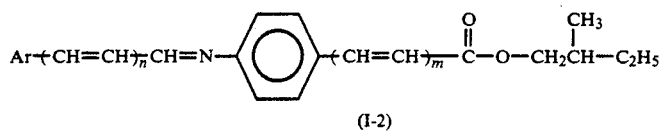
(I-2)
| Schiff Base Compound No. | n | m | Ar |
|---|---|---|---|
| 2 - 32 | 0 | 1 | 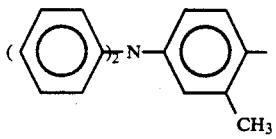 |
| 2 - 33 | 1 | 0 | 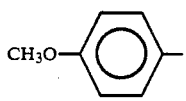 |
| 2 - 34 | 0 | 1 | 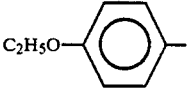 |
| 2 - 35 | 0 | 0 | 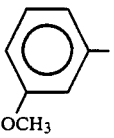 |
| 2 - 36 | 1 | 1 | 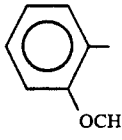 |
| 2 - 37 | 0 | 1 | 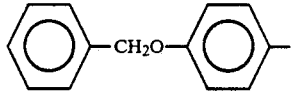 |
| 2 - 38 | 0 | 1 | 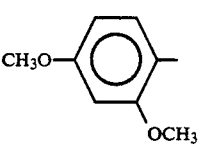 |
| 2 - 39 | 0 | 1 | 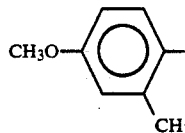 |
| 2 - 40 | 0 | 0 | 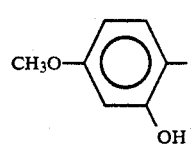 |

TABLE 2-continued
[Schiff base compounds having formula (I-2)
prepared by use of anilines of formula (III-2)]
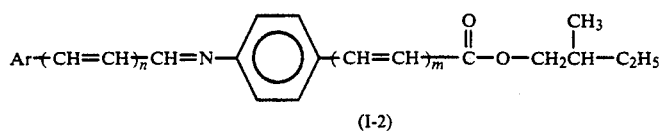
(I-2)
| Schiff Base Compound No. | n | m | Ar |
|---|---|---|---|
| 2 - 41 | 0 | 1 | CH₃O—⟨benzene⟩—, with OH |
| 2 - 42 | 0 | 0 | C₁₀H₂₁O—⟨benzene⟩—, with OH |
| 2 - 43 | 0 | 0 | CH₃CO(=O)—⟨benzene⟩— |
| 2 - 44 | 0 | 1 | CH₃S—⟨benzene⟩— |
| 2 - 45 | 0 | 0 | HO—⟨benzene⟩— |
| 2 - 46 | 0 | 0 | ⟨benzene⟩—, with OH |
| 2 - 47 | 0 | 1 | CH₃—⟨benzene⟩— |
| 2 - 48 | 0 | 1 | C₂H₅—⟨benzene⟩— |
| 2 - 49 | 0 | 1 | CH₃—⟨benzene⟩—, with OH |
| 2 - 50 | 0 | 0 | CH₃—⟨benzene⟩—, with Cl |

TABLE 2-continued
[Schiff base compounds having formula (I-2)
prepared by use of anilines of formula (III-2)]
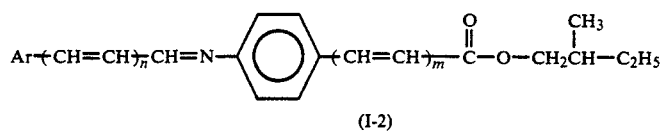
(I-2)
| Schiff Base Compound No. | n | m | Ar |
|---|---|---|---|
| 2 - 51 | 0 | 1 | phenyl |
| 2 - 52 | 1 | 1 | phenyl |
| 2 - 53 | 0 | 0 | biphenyl |
| 2 - 54 | 0 | 1 | biphenyl |
| 2 - 55 | 0 | 0 | $C_{10}H_{21}O$-biphenyl |
| 2 - 56 | 0 | 0 | Cl-phenyl |
| 2 - 57 | 0 | 1 | Cl-phenyl |
| 2 - 58 | 0 | 1 | 3,5-dichlorophenyl |
| 2 - 59 | 0 | 1 | Br-phenyl |
| 2 - 60 | 0 | 0 | $CH_3OC(O)$-phenyl |
| 2 - 61 | 0 | 1 | $CH_3OC(O)$-phenyl |

TABLE 2-continued
[Schiff base compounds having formula (I-2) prepared by use of anilines of formula (III-2)]
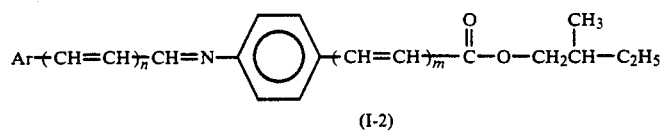
(I-2)
| Schiff Base Compound No. | n | m | Ar |
|---|---|---|---|
| 2 - 62 | 0 | 0 | NC—C₆H₄— |
| 2 - 63 | 0 | 0 | O₂N—C₆H₄— |
| 2 - 64 | 0 | 0 | naphthyl |
| 2 - 65 | 0 | 1 | naphthyl |
| 2 - 66 | 0 | 0 | 2-OCH₃-naphthyl |
| 2 - 67 | 0 | 1 | 4-OCH₃-naphthyl |
| 2 - 68 | 0 | 0 | 2-OH-naphthyl |
| 2 - 69 | 0 | 1 | 2-OH-naphthyl |
| 2 - 70 | 0 | 1 | anthryl |

TABLE 2-continued
[Schiff base compounds having formula (I-2)
prepared by use of anilines of formula (III-2)]
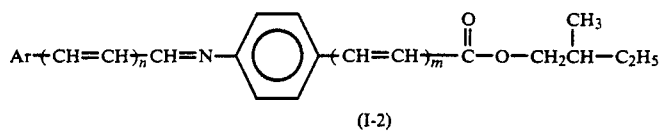
(I-2)
| Schiff Base Compound No. | n | m | Ar |
|---|---|---|---|
| 2 - 71 | 0 | 1 | 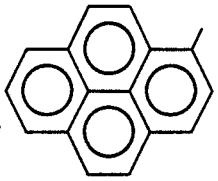 |
| 2 - 72 | 0 | 0 | 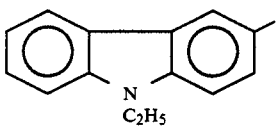 |
| 2 - 73 | 0 | 1 | 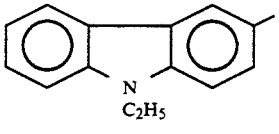 |
| 2 - 74 | 0 | 1 | 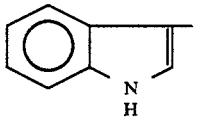 |
| 2 - 75 | 0 | 1 | 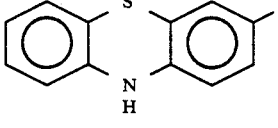 |
| 2 - 76 | 0 | 1 | 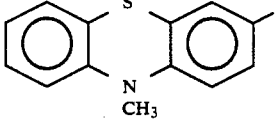 |
| 2 - 77 | 0 | 1 | 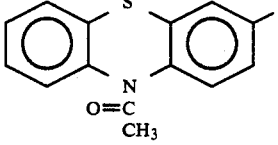 |
| 2 - 78 | 0 | 1 |  |
| 2 - 79 | 0 | 1 |  |

TABLE 3

[Schiff base compounds having formula (I-3) prepared by use of p-aminobenzoic acid(1-ethoxycarbonylethyl)ester

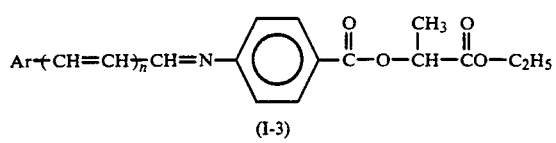

(I-3)

| Schiff Base Compound No. | n | Ar |
|---|---|---|
| 3 - 1 | 0 | (CH₃)₂N—⟨Ph⟩— |
| 3 - 2 | 0 | (C₂H₅)₂N—⟨Ph⟩— |
| 3 - 3 | 0 | (C₄H₉)₂N—⟨Ph⟩— |
| 3 - 4 | 1 | (CH₃)₂N—⟨Ph⟩— |
| 3 - 5 | 0 | (CH₃)₂N—⟨Ph(Cl)⟩— |
| 3 - 6 | 0 | (C₂H₅)₂N—⟨Ph(CH₃)⟩— |
| 3 - 7 | 0 | (⟨Ph⟩CH₂)₂N—⟨Ph⟩— |
| 3 - 8 | 0 | (CH₃—⟨Ph⟩—CH₂)₂N—⟨Ph⟩— |
| 3 - 9 | 0 | (Cl—⟨Ph⟩—CH₂)₂N—⟨Ph⟩— |
| 3 - 10 | 0 | (⟨Ph⟩CH₂)₂N—⟨Ph(CH₃)⟩— |

TABLE 3-continued

[Schiff base compounds having formula (I-3) prepared by use of p-aminobenzoic acid(1-ethoxycarbonylethyl)ester

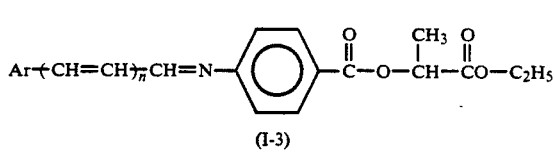

(I-3)

| Schiff Base Compound No. | n | Ar |
|---|---|---|
| 3 - 11 | 0 | (⟨Ph⟩CH₂)₂N—⟨Ph(OCH₃)⟩— |
| 3 - 12 | 0 | ⟨Ph⟩N(CH₃)—⟨Ph⟩— |
| 3 - 13 | 0 | ⟨Ph⟩N(C₂H₅)—⟨Ph⟩— |
| 3 - 14 | 0 | ⟨Ph⟩N(CH₂⟨Ph⟩)—⟨Ph⟩— |
| 3 - 15 | 0 | (CH₃O—⟨Ph⟩)₂N—⟨Ph⟩— |
| 3 - 16 | 0 | (CH₃—⟨Ph⟩)₂N—⟨Ph⟩— |
| 3 - 17 | 0 | (Cl—⟨Ph⟩)₂N—⟨Ph⟩— |
| 3 - 18 | 0 | (⟨Ph⟩)₂N—⟨Ph⟩— |
| 3 - 19 | 0 | (⟨Ph⟩)₂N—⟨Ph(CH₃)⟩— |

TABLE 3-continued

[Schiff base compounds having formula (I-3) prepared by use of p-aminobenzoic acid(1-ethoxycarbonylethyl)ester $$Ar(CH=CH)_{\overline{n}}CH=N-\text{C}_6H_4-CO-O-CH(CH_3)-CO-OC_2H_5 \quad (I-3)$$

| Schiff Base Compound No. | n | Ar |
|---|---|---|
| 3-20 | 0 | 4-CH₃O-C₆H₄-N(C₆H₅)-C₆H₄- |
| 3-21 | 0 | 4-CH₃-C₆H₄-N(C₆H₅)-C₆H₄- |
| 3-22 | 0 | 4-Cl-C₆H₄-N(C₆H₅)-C₆H₄- |
| 3-23 | 0 | 4-NC-C₆H₄-N(C₆H₅)-C₆H₄- |
| 3-24 | 0 | 4-CH₃O-C₆H₄- |
| 3-25 | 0 | 4-C₂H₅O-C₆H₄- |
| 3-26 | 0 | 4-C₄H₉O-C₆H₄- |
| 3-27 | 0 | 4-C₆H₁₃O-C₆H₄- |
| 3-28 | 0 | 4-C₈H₁₇O-C₆H₄- |
| 3-29 | 0 | 4-C₁₀H₂₁O-C₆H₄- |
| 3-30 | 0 | 3-CH₃O-C₆H₄- |
| 3-31 | 0 | 2-CH₃O-C₆H₄- |
| 3-32 | 0 | 4-(C₆H₅CH₂O)-C₆H₄- |
| 3-33 | 0 | 3,4-(CH₃O)₂-C₆H₃- |
| 3-34 | 0 | 3,4,5-(CH₃O)₃-C₆H₂- |
| 3-35 | 0 | 3-CH₃-4-CH₃O-C₆H₃- |
| 3-36 | 0 | 3-OH-4-CH₃O-C₆H₃- |
| 3-37 | 0 | 3-OH-4-C₆H₁₃O-C₆H₃- |

TABLE 3-continued

[Schiff base compounds having formula (I-3) prepared by use of p-aminobenzoic acid(1-ethoxycarbonylethyl)ester

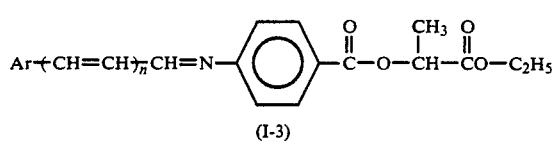

(I-3)

| Schiff Base Compound No. | n | Ar |
|---|---|---|
| 3 - 38 | 0 | 3-acetoxy-4-hydroxyphenyl (CH₃CO-O-C₆H₃(OH)-) |
| 3 - 39 | 0 | 4-(methylthio)phenyl (CH₃S-C₆H₄-) |
| 3 - 40 | 0 | 4-hydroxyphenyl (HO-C₆H₄-) |
| 3 - 41 | 0 | 2-hydroxyphenyl |
| 3 - 42 | 0 | 4-methylphenyl (CH₃-C₆H₄-) |
| 3 - 43 | 0 | 4-ethylphenyl (C₂H₅-C₆H₄-) |
| 3 - 44 | 0 | 3-methylphenyl |
| 3 - 45 | 0 | 2-methylphenyl |
| 3 - 46 | 0 | 3-methyl-4-hydroxyphenyl |

TABLE 3-continued

[Schiff base compounds having formula (I-3) prepared by use of p-aminobenzoic acid(1-ethoxycarbonylethyl)ester

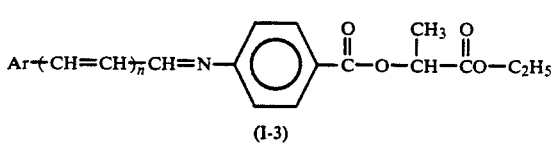

(I-3)

| Schiff Base Compound No. | n | Ar |
|---|---|---|
| 3 - 47 | 0 | 3-methyl-4-chlorophenyl |
| 3 - 48 | 0 | 4-biphenylyl |
| 3 - 49 | 0 | 4'-decyloxy-4-biphenylyl (C₁₀H₂₁O-C₆H₄-C₆H₄-) |
| 3 - 50 | 0 | phenyl |
| 3 - 51 | 1 | phenyl |
| 3 - 52 | 0 | 4-chlorophenyl (Cl-C₆H₄-) |
| 3 - 53 | 0 | 3-chlorophenyl |
| 3 - 54 | 0 | 4-bromophenyl (Br-C₆H₄-) |
| 3 - 55 | 0 | 4-(methoxycarbonyl)phenyl (CH₃OC(O)-C₆H₄-) |
| 3 - 56 | 0 | 4-(ethoxycarbonyl)phenyl (C₂H₅OC(O)-C₆H₄-) |
| 3 - 57 | 0 | 4-cyanophenyl (NC-C₆H₄-) |

TABLE 3-continued

[Schiff base compounds having formula (I-3) prepared by use of p-aminobenzoic acid(1-ethoxycarbonylethyl)ester

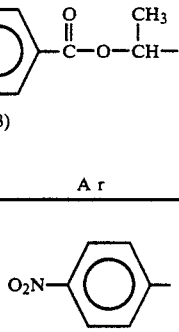

(I-3)

| Schiff Base Compound No. | n | Ar |
|---|---|---|
| 3 - 58 | 0 | 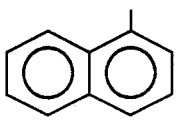 |
| 3 - 59 | 0 | 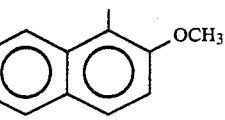 |
| 3 - 60 | 0 | 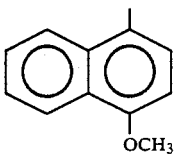 |
| 3 - 61 | 0 | 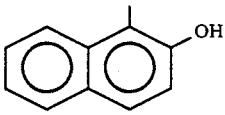 |
| 3 - 62 | 0 | 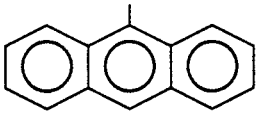 |
| 3 - 63 | 0 | 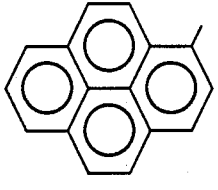 |
| 3 - 64 | 0 | 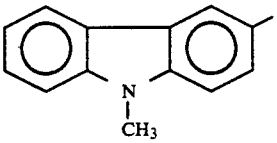 |
| 3 - 65 | 0 | 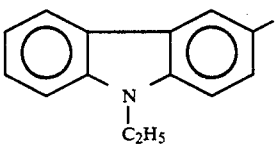 |
| 3 - 66 | 0 | 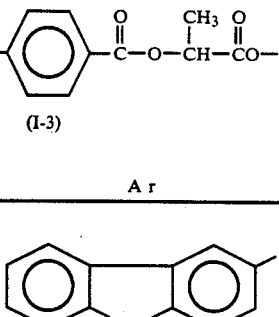 |
| 3 - 67 | 0 | 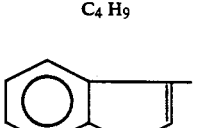 |
| 3 - 68 | 0 | 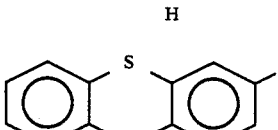 |
| 3 - 69 | 0 | 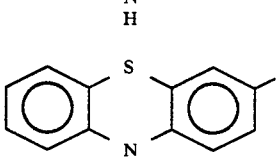 |
| 3 - 70 | 0 | 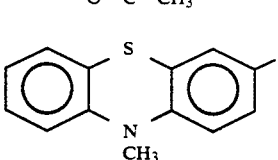 |
| 3 - 71 | 0 | 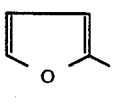 |
| 3 - 72 | 0 | 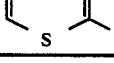 |
| 3 - 73 | 0 | |

The present invention will now be explained in more detail with reference to the following examples, which are given for illustration of the invention and are not intended to be limiting thereof.

EXAMPLE 1-1

Preparation of Schiff Base Compound No. 1—1 (optical active p-(p'-N,N-dimethylaminobenzylideneamino)benzoic acid (N'-2-methylbutyl)amide Step 1-1-A. Preparation of optical active p-nitrobenzoic acid(N-2-methylbutyl)amide having formula (VI-1)

17.43 g (0.2 mol) of commercially available (S)2-methyl-1-butylamine was dissolved in 100 ml of pyridine. While cooling this solution, 40.83 g (0.22 mol) of commercially available 4-nitrobenzoic acid chloride having formula (IV-1) was added thereto. The thus obtained mixture was stirred at 50° to 60° C. for 2 hours to complete the reaction.

After the completion of the reaction, the above mixture was poured on 1 l of cold water and neutralized with 6N HCl with stirring. A crystalline product separated out in the reaction mixture. The crystalline product was separated from the reaction mixture by filtration, washed with water and dried, so that a crude product was obtained. The thus obtained crude product was recrystallized from ethanol, whereby 30.04 g of pure optical active p-nitrobenzoic acid (N-2-methylbutyl)amide having formula (VI-1) was obtained.

The melting point and optical rotation of the obtained product were as follows:
Melting point: 78.0° to 79.0° C.
Optical rotation $[\alpha]^D$: (+)5.74°.

The results of the elemental analysis of the thus obtained product were as follows:

|  | % C | % H | % N |
|---|---|---|---|
| Calculated | 61.00 | 6.83 | 11.86 |
| Found | 60.89 | 6.82 | 11.75 |

Step 1-1-B. Preparation of optical active p-aminobenzoic acid (N'-2-methylbutyl)amide having formula (III-1)

28.35 g (0.12 mol) of optical active p-nitrobenzoic acid (N-2-methylbutyl)amide having formula (VI-1) obtained in the above step 1-1-A was dissolved in 300 ml of 1,4-dioxane. This solution was subjected to catalytic hydrogenation in the presence of 0.9 g of Pd-C at room temperature.

After the completion of the hydrogenation reaction, the catalyst of Pd-C was removed by filtration and the solvent was distilled away from the reaction mixture. The residue was recrystallized from toluene, whereby 18.92 g of pure optical active p-aminobenzoic acid (N'-2-methylbutyl)amide having formula (III-1) was obtained.

The melting point and optical rotation of the obtained product were as follows:
Melting point: 96.5° to 97.5° C.
Optical rotation $[\alpha]^D$: (+)6.24°.

The results of the elemental analysis of the thus obtained product were as follows:

|  | % C | % H | % N |
|---|---|---|---|
| Calculated | 69.87 | 8.80 | 13.58 |
| Found | 69.78 | 8.91 | 13.56 |

Figure 2:
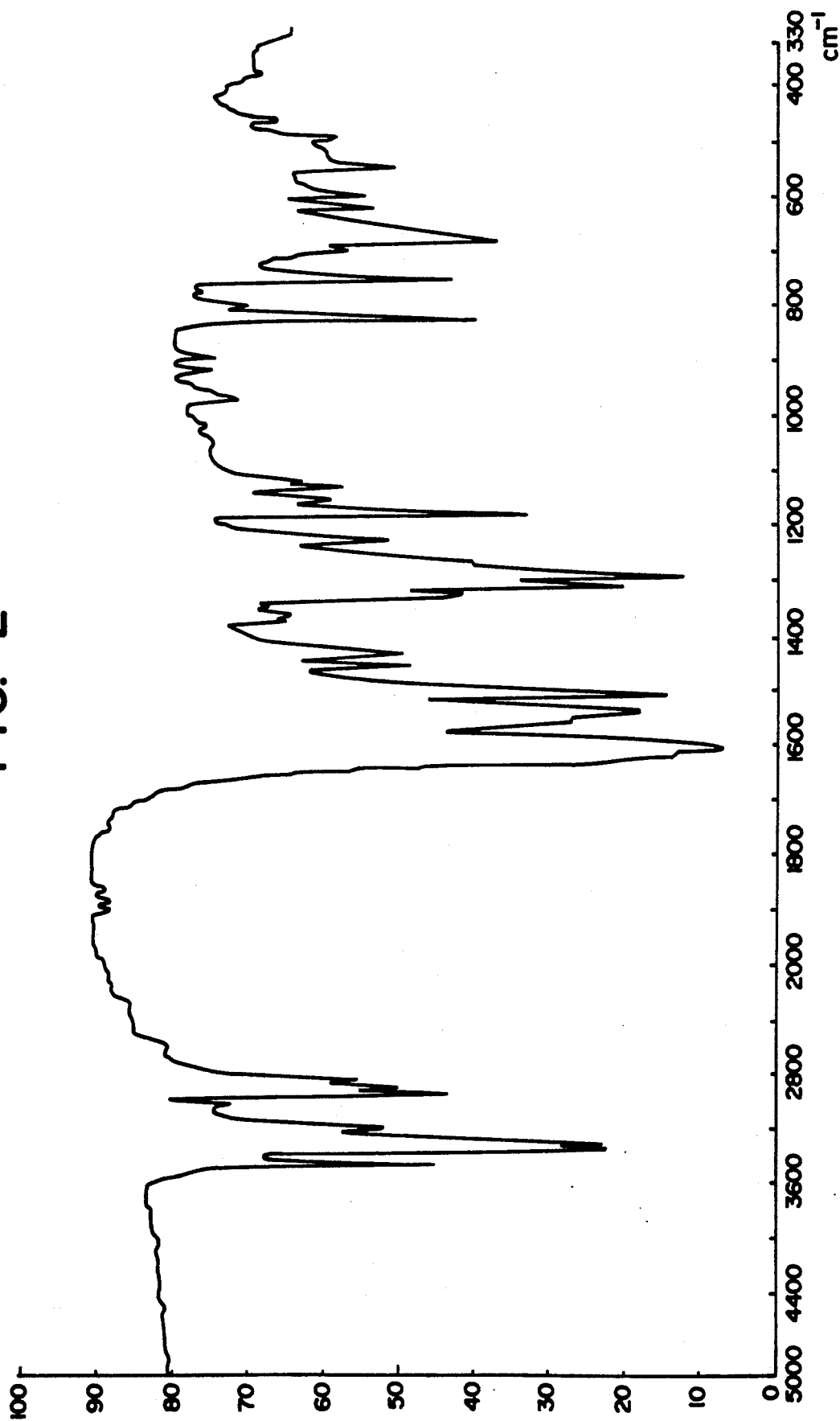
FIG. 2 is an infrared absorption spectrum of optical active p-aminobenzoic acid (N'-2-methylbutyl)amide obtained in Step 1-1-B of Example 1—1.

FIG. 2 shows an infrared spectrum of the above obtained optical active p-aminobenzoic acid (N'-2-methylbutyl)amide having formula (III-1), taken by use of a KBr tablet.

Step 1-1-C. Preparation of optical active p-(p'-N,N-dimethylaminobenzylideneamino)benzoic acid (N'-2-methylbutyl)amide having formula (I-1) = Schiff base compound No. 1—1

2.06 g (0.01 mol) of optical active p-aminobenzoic acid (N'-2-methylbutyl)amide having formula (III-1) obtained in the above step 1-1-B and 1.49 g (0.001 mol) of commercially available p-N,N-dimethylaminobenzaldehyde were dissolved in 100 ml of absolute alcohol. This solution was stirred at room temperature for 6 hours and allowed to stand overnight, so that a product was precipitated. The precipitated product was recrystallized from absolute alcohol, whereby 1.25 g of pure optical active p-(p'-N,N-dimethylaminobenzylideneamino)benzoic acid (N'-2-methylbutyl)amide (Schiff base compound No. 1—1) was obtained.

Figure 3:
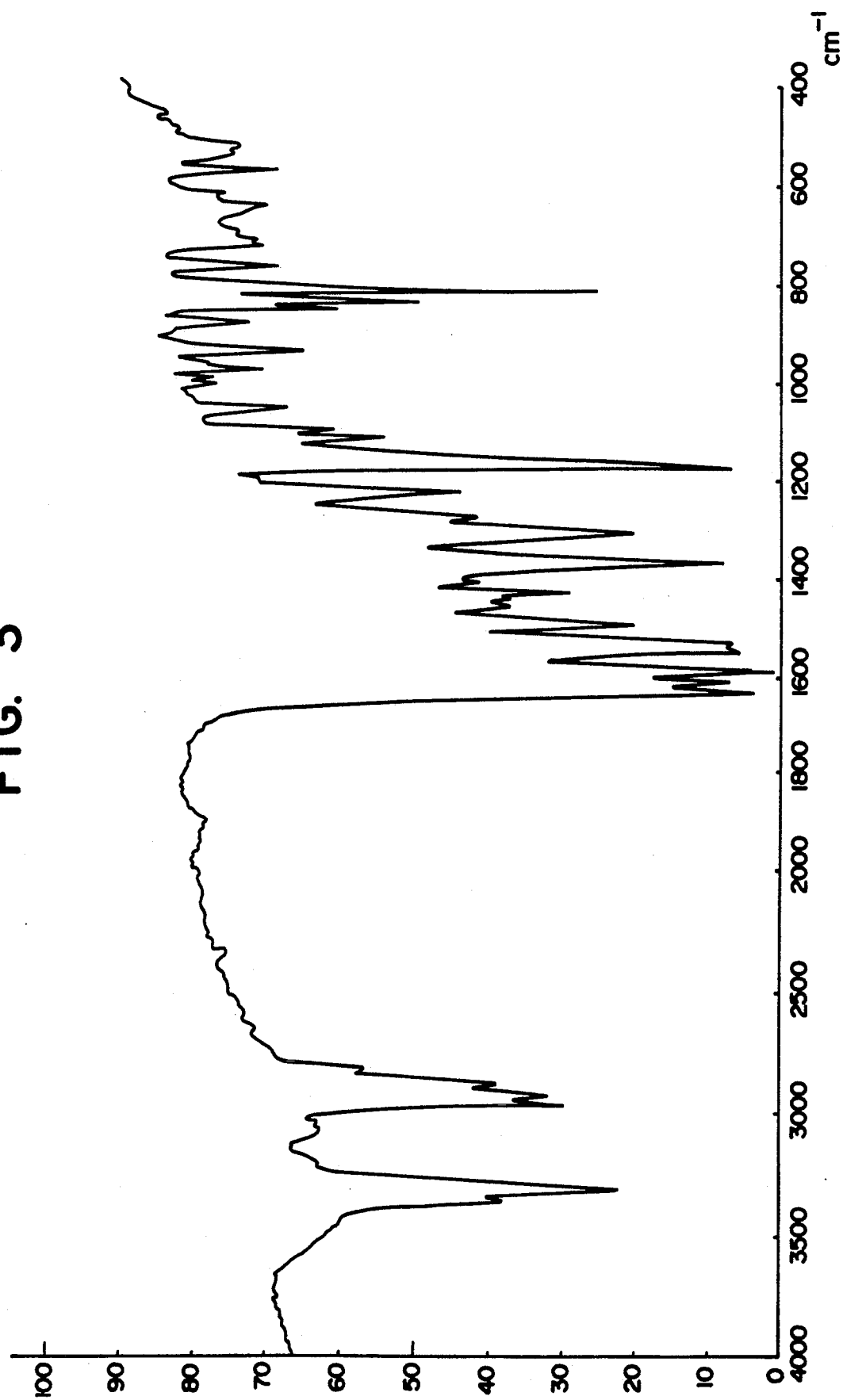
FIG. 3 is an infrared absorption spectrum of optical active p-(p'-N,N-dimethylaminobenzylideneamino)benzoic acid (N'-2-methylbutyl)amide obtained in Step 1-1-C of Example 1—1.

FIG. 3 shows an infrared spectrum of the above obtained optical active p-(p'-N,N-dimethylaminobenzylideneamino)benzoic acid (N'-2-methylbutyl)amide (Schiff base compound No. 1—1), taken by use of a KBr tablet.

EXAMPLES 1-2 to 1-13

The procedure for preparation of Schiff base compound No. 1—1 employed in Example 1—1 was repeated except that p-N,N-dimethylaminobenzaldehyde used in the step 1-1-C of Example 1—1 was replaced by the respective aldehydes having formula (II) as shown in Table 4, whereby Schiff base compounds of formula (I-1) according to the present invention were obtained.

The melting points and the results of the elemental analysis of the thus obtained Schiff base compounds of formula (I-1) according to the present invention are given in Table 4.

TABLE 4

| Example No. | Schiff Base Compound No. | Formula (I-1) n | Ar | Melting Point (C.°) | Elemental Analysis Found (%) | Counted (%) |
|---|---|---|---|---|---|---|
| 1 - 1 | 1 - 1 | 0 | 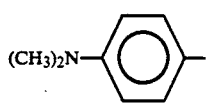 | 186.0~187.5 | C 74.77<br>H 8.17<br>N 12.44 | 74.74<br>8.07<br>12.45 |
| 1 - 2 | 1 - 4 | 1 | 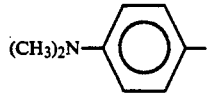 | 192.5~193.5 | C 76.03<br>H 8.11<br>N 11.57 | 76.00<br>8.04<br>11.56 |
| 1 - 3 | 1 - 7 | 0 | 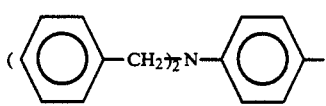 | Oily Substance | C 81.09<br>H 7.18<br>N 8.50 | 80.95<br>7.21<br>8.58 |

TABLE 4-continued

| Example No. | Schiff Base Compound No. | Formula (I-1) n | Ar | Melting Point (C.°) | Elemental Analysis | Found (%) | Counted (%) |
|---|---|---|---|---|---|---|---|
| 1 - 4 | 1 - 14 | 0 | 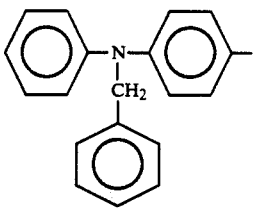 | Oily Substance | C<br>H<br>N | 80.75<br>6.81<br>8.93 | 80.81<br>6.99<br>8.84 |
| 1 - 5 | 1 - 18 | 0 | 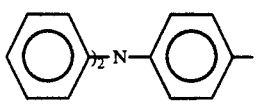 | 128.0~129.5 | C<br>H<br>N | 80.51<br>6.87<br>9.12 | 80.66<br>6.77<br>9.10 |
| 1 - 6 | 1 - 27 | 0 | 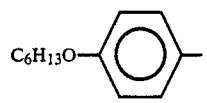 | 143.2~144.0 | C<br>H<br>N | 76.21<br>8.81<br>7.19 | 76.10<br>8.69<br>7.10 |
| 1 - 7 | 1 - 28 | 0 | 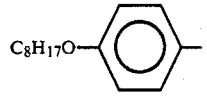 | 147.5~148.0 | C<br>H<br>N | 76.66<br>9.03<br>6.71 | 76.74<br>9.06<br>6.63 |
| 1 - 8 | 1 - 29 | 0 | 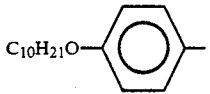 | 144.5~145.0 | C<br>H<br>N | 77.19<br>9.45<br>6.17 | 77.29<br>9.39<br>6.22 |
| 1 - 9 | 1 - 49 | 0 | 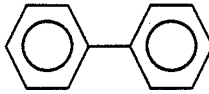 | 216.0~216.8 | C<br>H<br>N | 81.09<br>7.19<br>7.53 | 81.05<br>7.07<br>7.56 |
| 1 - 10 | 1 - 52 | 0 | 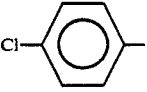 | 138.5~139.5 | C<br>H<br>N | 69.51<br>6.29<br>8.55 | 69.40<br>6.44<br>8.52 |
| 1 - 11 | 1 - 56 | 0 | 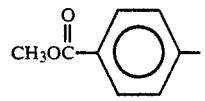 | 147.5~148.5 | C<br>H<br>N | 71.62<br>6.80<br>7.82 | 71.57<br>6.86<br>7.95 |
| 1 - 12 | 1 - 63 | 0 | 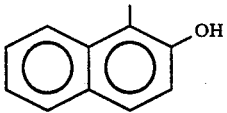 | 166.5~167.5 | C<br>H<br>N. | 76.53<br>6.70<br>7.83 | 76.64<br>6.71<br>7.77 |
| 1 - 13 | 1 - 67 | 0 | 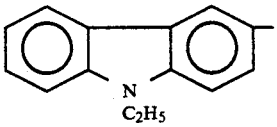 | 169.5~170.5 | C<br>H<br>N | 78.89<br>7.22<br>10.27 | 78.80<br>7.10<br>10.21 |

The nonlinear optical properties of the Schiff base compound No. 1-49 according to the present invention obtained in Examples 1-9 were evaluated. More specifically, the intensity of the second higher harmonic generation (SHG), one of the representative nonlinear optical properties, was measured in accordance with a method reported in J. Apply. Phys. 39,3798 (1968) by S. K. Kurts and T. T. Perry. According to this method, the intensity of the second higher harmonic generation of the Schiff base compound No. 1–49, which is observed when a laser beam having a strong light intensity is applied to the Schiff base compound in the powdered form, is measured in comparison with the intensity of a reference material. The nonlinear optical properties of the Schiff base compound can be approximately evaluated by this method.

In this measurement, a $Nd^+$(neodymium): YAG (yttrium aluminum garnet) laser having an output energy of 250 mJ/pulse and a pulse width of 20 ns was employed as a light source. The wavelength of the YAG laser was 1.064 μm. When the YAG laser beam was applied to the optical active compound, the second higher harmonic generation of 523 nm was obtained in a green color. Since the powdered Schiff base compound was placed in the center of a silica glass cell and the YAG laser beam was projected onto the Schiff base compound through a small hole on the cell, the second higher harmonic generation was scattered in the cell. The intensity of the second higher harmonic generation was observed at two positions in the cell, one was on the YAG laser side and the other was on the opposite side. To detect the SHG intensity of the Schiff base compound, a commercially available photomultiplier was used, which was equipped with an interference filter, thereby picking up only the second higher harmonic generation of 532 nm, with other laser beams being cut off by means of an infrared absorption filter.

The powdered Schiff base compound according to the present invention was not sieved before the measurement. As the reference material, finely-divided urea having an average particle diameter of about 100 μm was employed.

The results of the measurement are shown in Table 5.

TABLE 5

| Schiff Base Compound No. | Intensity of Secondary Higher Harmonic Generation (relative to urea) |
| --- | --- |
| No. 1-49 | 0.11 |

The Schiff base compounds according to the present invention obtained in Examples 1—1 to 1-12 are effective as nonlinear optical materials. For example, the Schiff base compounds according to the present invention can be used as a second higher harmonic generation device as shown in FIG. 1 by preparing the single crystal of the above-mentioned Schiff base compounds. In FIG. 1, the second higher harmonic generation device is designed in such a fashion that when a laser beam of a semiconductor laser 1 is applied to a single crystal of Schiff base compound 2 according to the present invention, the secondary higher harmonic generation can be obtained.

EXAMPLE 2-1

Preparation of Schiff Base Compound No. 2-1 (optical active p-(p'-N,N-dimethylaminobenzylideneamino)benzoic acid-2-methylbutyl ester 2.07 g (0.01 mol) of optical active p-aminobenzoic acid-2-methylbutyl ester having formula (III-2) and 1.49 g (0.01 mol) of commercially available p-N,N-dimethylaminobenzaldehyde were dissolved in 100 ml of absolute alcohol. This solution was stirred at room temperature for 6 hours and allowed to stand overnight, so that a product was precipitated. The precipitated product was recrystallized from absolute ethanol, whereby 2.25 g of pure optical active p-(p'-N,N-dimethylaminobenzylideneamino)benzoic acid-2-methylbutyl ester (Schiff base compound No. 2-1) was obtained.

The thus obtained Schiff base compound No. 2-1 has a melting point of 70.5° to 71.5° C.

Figure 4:
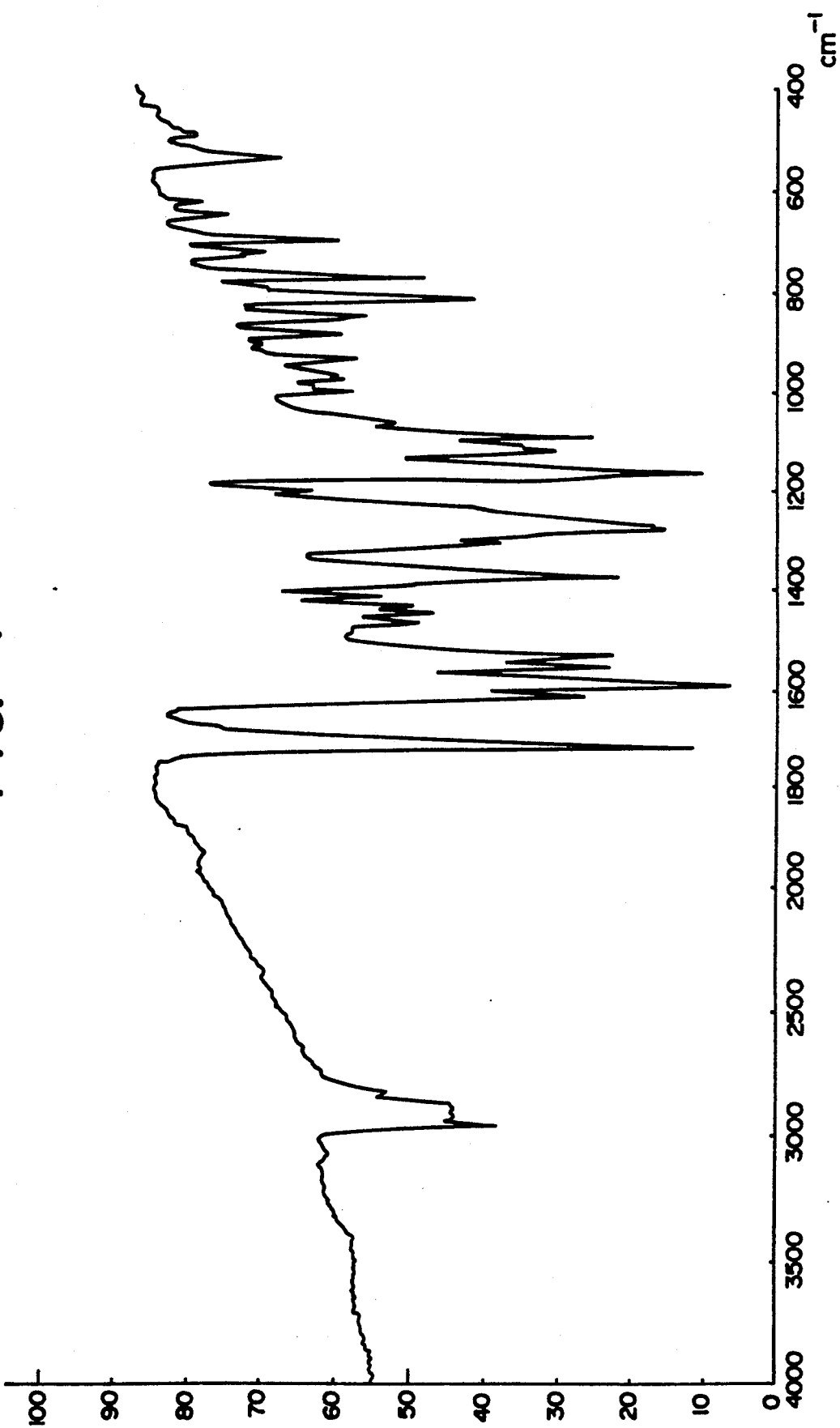
FIG. 4 is an infrared absorption spectrum of optical active p-(p'-N,N-dimethylaminobenzylideneamino)benzoic acid-2-methylbutyl ester obtained in Example 2-1.

FIG. 4 shows an infrared spectrum of the above obtained optical active p-(p'-N,N-dimethylaminobenzylideneamino)benzoic acid-2-methylbutyl ester (Schiff base compound No. 2-1), taken by use of a KBr tablet.

EXAMPLE 2—2 TO 2-19

The procedure for preparation of Schiff base compound No. 2-1 employed in Example 2-1 was repeated except that p-N,N-dimethylaminobenzaldehyde and p-aminobenzoic acid-2-methylbutyl ester used in Example 2-1 were respectively replaced by the aldehydes having formula (II) and anilines having formula (III-2) as shown in Table 6, whereby Schiff base compounds of formula (I-2) according to the present invention were obtained. The melting point and the results of the elemental analysis of the thus obtained Schiff base compounds of formula (I-2) according to the present invention are shown in Table 6.

TABLE 6

| Example No. | Schiff Base Compound No. | Formula (I-2) | | | Melting Point (°C.) (Transparent Point) | Elemental Analysis | | |
| --- | --- | --- | --- | --- | --- | --- | --- | --- |
| | | n | m | Ar | | | Found (%) | Counted (%) |
| 2-1 | 2-1 | 0 | 0 | (CH₃)₂N—⟨phenyl⟩— 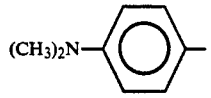 | 70.5~71.5 | C<br>H<br>N | 74.54<br>7.72<br>8.33 | 74.53<br>7.74<br>8.28 |
| 2-2 | 2-2 | 1 | 0 | (CH₃)₂N—⟨phenyl⟩— 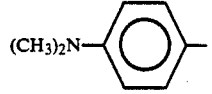 | 135.0~136.0 | C<br>H<br>N | 75.65<br>7.67<br>7.85 | 75.79<br>7.74<br>7.77 |
| 2-3 | 2-3 | 0 | 1 | (CH₃)₂N—⟨phenyl⟩— 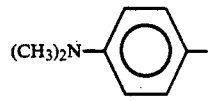 | (129.0) | C<br>H<br>N | 75.72<br>7.78<br>7.75 | 75.79<br>7.74<br>7.77 |
| 2-4 | 2-4 | 1 | 1 | (CH₃)₂N—⟨phenyl⟩— 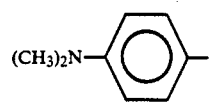 | (160.5) | C<br>H<br>N | 76.95<br>7.84<br>7.16 | 76.89<br>7.74<br>7.17 |

TABLE 6-continued

| Example No. | Schiff Base Compound No. | Formula (I-2) n | m | Ar | Melting Point (°C.) (Transparent Point) | Elemental Analysis Found (%) | Counted (%) |
|---|---|---|---|---|---|---|---|
| 2 - 5 | 2 - 13 | 0 | 1 | (C₆H₅-CH₂)₂N-C₆H₄- | 53.0~54.5 | C 81.30 H 6.91 N 5.41 | 81.36 7.02 5.42 |
| 2 - 6 | 2 - 26 | 0 | 1 | (C₆H₅)₂N-C₆H₄- | Oily Substance | C 79.91 H 6.32 N 5.30 | 80.12 6.60 5.73 |
| 2 - 7 | 2 - 40 | 0 | 0 | CH₃O-C₆H₃(OH)- | 81.0~82.0 | C 70.21 H 6.72 N 3.93 | 70.36 6.79 4.10 |
| 2 - 8 | 2 - 41 | 0 | 1 | CH₃O-C₆H₃(OH)- | 143.0~144.0 | C 71.83 H 6.80 N 3.68 | 71.91 6.86 3.81 |
| 2 - 9 | 2 - 42 | 0 | 0 | C₁₀H₂₁O-C₆H₃(OH)- | (84.0) | C 74.33 H 8.76 N 2.91 | 74.48 8.84 3.00 |
| 2 - 10 | 2 - 53 | 0 | 0 | C₆H₅-C₆H₄- | (109.0) | C 80.95 H 6.74 N 3.82 | 80.83 6.78 3.77 |
| 2 - 11 | 2 - 54 | 0 | 1 | C₆H₅-C₆H₄- | (196.0) | C 81.52 H 6.95 N 3.45 | 81.58 6.85 3.52 |
| 2 - 12 | 2 - 55 | 0 | 0 | C₁₀H₂₁O-C₆H₄-C₆H₄- | (201.0) | C 79.59 H 8.74 N 2.56 | 79.66 8.60 2.65 |
| 2 - 13 | 2 - 56 | 0 | 0 | Cl-C₆H₄- | 58.0~58.5 | C 69.21 H 6.18 N 4.13 | 69.19 6.11 4.25 |
| 2 - 14 | 2 - 57 | 0 | 1 | Cl-C₆H₄- | (70.0) | C 70.91 H 6.37 N 3.86 | 70.88 6.23 3.94 |
| 2 - 15 | 2 - 60 | 0 | 0 | CH₃OC(O)-C₆H₄- | 83.0~84.0 | C 71.33 H 6.48 N 3.95 | 71.37 6.56 3.94 |
| 2 - 16 | 2 - 61 | 0 | 1 | CH₃OC(O)-C₆H₄- | (119.5) | C 72.70 H 6.59 N 3.67 | 72.80 6.64 3.69 |

TABLE 6-continued

| Example No. | Schiff Base Compound No. | Formula (I-2) n | m | Ar | Melting Point (°C.) (Transparent Point) | Elemental Analysis Found (%) | Counted (%) |
|---|---|---|---|---|---|---|---|
| 2 - 17 | 2 - 68 | 0 | 0 | [naphthyl-OH structure] | 136.0~137.0 | C 76.57<br>H 6.31<br>N 6.73 | 76.43<br>6.41<br>3.88 |
| 2 - 18 | 2 - 69 | 0 | 1 | [naphthyl-OH structure] | 144.5~145.5 | C 77.62<br>H 6.45<br>N 3.61 | 77.50<br>6.50<br>3.62 |
| 2 - 19 | 2 - 73 | 0 | 1 | [carbazole with N-C$_2$H$_5$ structure] | 139.0~140.5 | C 79.48<br>H 7.08<br>N 6.25 | 79.42<br>6.90<br>6.39 |

The nonlinear optical properties of the Schiff base compounds No. 2-13, No. 2-55, No. 2-56 and No. 2-60 according to the present invention were evaluated in the same manner as previously mentioned.

The results of the measurement is given in Table 7.

TABLE 7

| Schiff Base Compound No. | Intensity of Secondary Higher Harmonic Generation (relative to urea) |
|---|---|
| No. 2-13 | 1.33 |
| No. 2-55 | 0.44 |
| No. 2-56 | 1.11 |
| No. 2-60 | 1.00 |

The Schiff base compounds according to the present invention obtained in Examples 2—1 to 2—22 are effective as nonlinear optical materials.

EXAMPLE 3-1

Preparation of Schiff Base Compound No. 3-1 (optical active p-(p'-N,N-dimethylaminobenzylideneamino)benzoic acid(1-ethoxycarbonylethyl)ester 3-1-A. Preparation of optical active p-nitrobenzoic acid(1-ethoxycarbonylethyl)ester having formula (VI-3)

23.63 g (0.2 mol) of commercially available L-ethyl lactate having formula (V-3) was dissolved in a mixed solvent of 50 ml of pyridine and 400 ml of toluene. While cooling this solution, 40.83 g (0.22 mol) of commercially available 4-nitrobenzoic acid chloride having formula (IV-3) was added thereto. The thus obtained mixture was stirred at 50° to 60° C. for 2 hours to complete the reaction.

After the completion of the reaction, the above mixture was poured upon 1 l of cold water and vigorously stirred. A toluene layer was formed in the reaction mixture. The toluene layer was separated, washed with 6N HCl and then washed water until the toluene layer became neutral. The toluene layer was dried by use of magnesium sulfuric anhydride and the toluene was distilled off. The residue was recrystallized from ethanol, whereby 43.10 g of pure optical active p-nitrobenzoic acid (1-ethoxycarbonylethyl) ester having formula (VI-3) was obtained.

The melting point and optical rotation of the obtained product were as follows:

Melting point: 41.3° to 42.0° C.

Optical rotation $[\alpha]^D$: (+)18.00°.

The results of the elemental analysis of the thus obtained product were as follows:

| | % C | % H | % N |
|---|---|---|---|
| Calculated | 53.82 | 4.90 | 5.24 |
| Found | 53.82 | 4.81 | 5.19 |

Step 3-1-B. Preparation of optical active p-aminobenzoic acid(1-ethoxycarbonylethyl)ester having formula (III-3)

32.07 g (0.12 mol) of optical active p-nitrobenzoic acid (1-ethoxycarbonylethyl)ester having formula (VI-3) obtained in the above step 3-1-A was dissolved in 300 ml of 1,4-dioxane. This solution was subjected to catalytic hydrogeneration in the presence of 0.9 g of Pd-C at room temperature.

After the completion of the hydrogeneration reaction, the catalyst of Pd-C was removed by filtration and the solvent was distilled away from the reaction solution. The residue was distilled under reduced pressure and the distillate at 180° C. to 182° C. (1 mmHg) was separated, whereby 20.33 g of pure optical active p-aminobenzoic acid (1-ethoxycarbonylethyl)ester having formula (III-3) was obtained.

The optical rotation of the obtained product was as follows:

Optical rotation $[\alpha]^D$: (+)48.35°.

The results of the elemental analysis of the thus obtained product were as follows:

| | % C | % H | % N |
|---|---|---|---|
| Calculated | 60.75 | 6.37 | 5.90 |
| Found | 60.72 | 6.29 | 5.90 |

Figure 5:
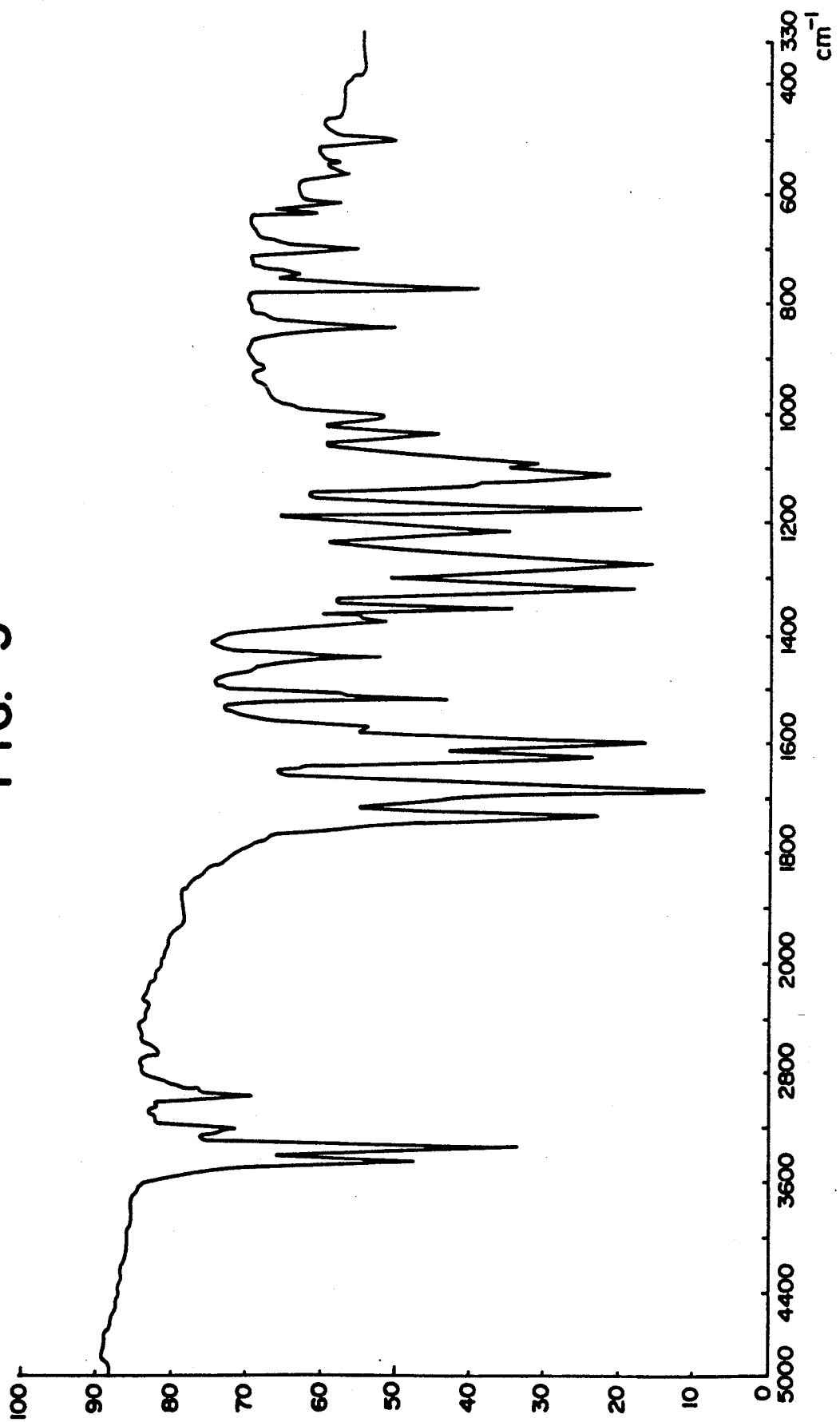
FIG. 5 is an infrared absorption spectrum of optical active p-aminobenzoic acid (1-ethoxycarbonylethyl)ester obtained in Step 3-1-B of Example 3-1.

FIG. 5 shows an infrared spectrum of the above obtained optical active p-aminobenzoic acid(1-ethoxycarbonylethyl) ester having formula (III-3), taken by use of a KBr tablet.

Step 3-1-C. Preparation of optical active p-(p'-N,N-dimethylaminobenzylideneamino)benzoic acid (1-ethoxycarbonylethyl)ester having formula (I-3)=Schiff base compound No. 3-1

2.37 g (0.01 mol) of optical active p-aminobenzoic acid(1-ethoxycarbonylethyl)ester having formula (III-3) obtained in the above step 3-1-B and 1.49 g (0.01 mol) of commercially available p-N,N-dimethylaminobenzaldehyde were dissolved in 100 ml of absolute alcohol. This solution was stirred at room temperature for 6 hours and allowed to stand overnight, so that a product was precipitated. The precipitated product was recrystallized from absolute alcohol, whereby 1.69 g of pure optical active p-(p'-N,N-imethylaminobenzylideneamino)benzoic acid (1-ethoxycarbonylethyl)ester (Schiff base compound No. 3-1) was obtained.

Figure 6:
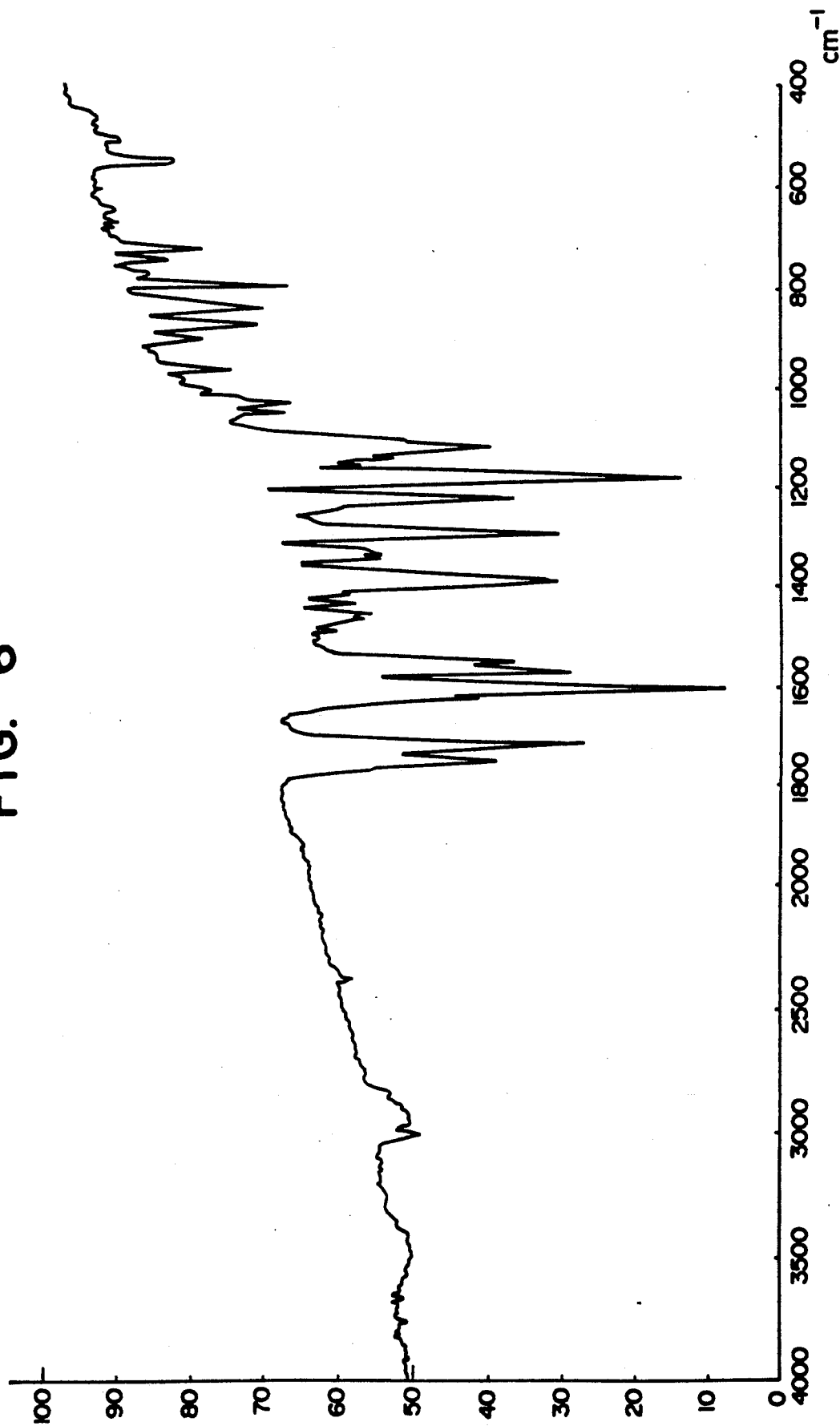
FIG. 6 is an infrared absorption spectrum of optical active p-(p'-N,N-dimethylaminobenzylideneamino)benzoic acid (1-ethoxycarbonylethyl)ester obtained in Step 3-1-C of Example 3-1.

FIG. 6 shows an infrared spectrum of the above obtained optical active Schiff base compound No. 3-1, taken by use of a KBr tablet.

EXAMPLES 3-2 TO 3-13

The procedure for preparation of Schiff base compound No. 3-1 employed in Example 3-1 was repeated except that p-N,N-dimethylaminobenzaldehyde used in the step 3-1-C of Example 3-1 was replaced by the respective aldehydes having formula (II) as shown in Table 8, whereby Schiff base compounds of formula (I-3) according to the present invention were obtained.

The melting points (or transparent points) and the results of the elemental analysis of the thus obtained Schiff base compounds of formula (I-3) according to the present invention are shown in Table 8.

TABLE 8

| Example No. | Schiff Base Compound No. | Formula (I-3) n | Ar | Melting Point (°C.) (Transparent Point) | Elemental Analysis | Found (%) | Counted (%) |
| --- | --- | --- | --- | --- | --- | --- | --- |
| 3-1 | 3-1 | 0 | 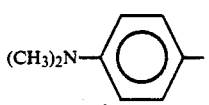 | 136.0~137.5 | C H N | 68.43 6.59 7.59 | 68.46 6.57 7.60 |
| 3-2 | 3-4 | 1 | 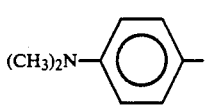 | 140.5~141.5 | C H N | 69.93 6.72 7.11 | 70.03 6.64 7.10 |
| 3-3 | 3-18 | 0 | 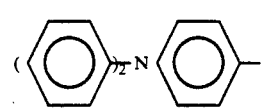 | 127.0~128.5 | C H N | 75.39 5.88 5.49 | 75.59 5.73 5.69 |
| 3-4 | 3-27 | 0 | 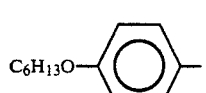 | 60.0~60.5 | C H N | 70.64 7.12 3.29 | 70.57 7.34 3.29 |
| 3-5 | 3-28 | 0 | 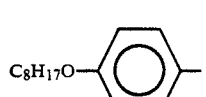 | 55.5~56.5 | C H N | 71.46 5.68 3.15 | 71.50 7.78 3.09 |
| 3-6 | 3-29 | 0 | 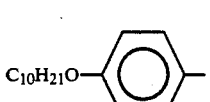 | 58.3~59.5 | C H N | 72.44 8.26 3.05 | 72.32 8.16 2.91 |
| 3-7 | 3-36 | 0 | 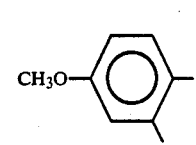 | 102.5~103.5 | C H N | 64.71 5.75 3.92 | 64.68 5.70 3.77 |
| 3-8 | 3-48 | 0 | 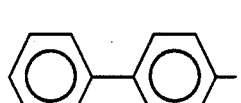 | (146.0) | C H N | 74.77 5.64 3.51 | 74.80 5.78 3.49 |
| 3-9 | 3-49 | 0 | 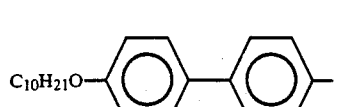 | (90.5) | C H N | 75.31 7.92 2.40 | 75.37 7.77 2.51 |

TABLE 8-continued

| Example No. | Schiff Base Compound No. | Formula (I-3) n | Ar | Melting Point (°C.) (Transparent Point) | Elemental Analysis Found (%) | Counted (%) |
|---|---|---|---|---|---|---|
| 3 - 10 | 3 - 52 | 0 | Cl—⟨phenyl⟩— | 97.5~98.0 | C 63.42<br>H 5.03<br>N 3.93 | 63.43<br>5.04<br>3.89 |
| 3 - 11 | 3 - 55 | 0 | $CH_3OC(=O)$—⟨phenyl⟩— | 94.0~95.0 | C 65.68<br>H 5.55<br>N 3.72 | 65.79<br>5.52<br>3.65 |
| 3 - 12 | 3 - 62 | 0 | 2-hydroxynaphthyl | 98.0~99.5 | C 70.69<br>H 5.44<br>N 3.65 | 70.58<br>5.41<br>3.58 |
| 3 - 13 | 3 - 66 | 0 | N-ethylcarbazolyl | | C 73.55<br>H 5.62<br>N 5.98 | 73.29<br>5.92<br>6.33 |

The nonlinear optical properties of the Schiff base compounds No. 3-1, No. 3-4, No. 3-62, No. 3-27, No. 3-36, No. 3-49, No. 3-52 and No. 3-55 according to the present invention were evaluated in the same manner as previously described.

The results of the measurement are given in Table 9

TABLE 9

| Schiff Base Compound No. | Intensity of Secondary Higher Harmonic Generation (relative to urea) |
|---|---|
| No. 3-1 | 0.83 |
| No. 3-4 | 0.15 |
| No. 3-62 | 0.20 |
| No. 3-27 | 0.30 |
| No. 3-36 | 1.50 |
| No. 3-49 | 0.30 |
| No. 3-52 | 0.20 |
| No. 3-55 | 0.10 |

The Schiff base compounds according to the present invention obtained in Examples 3-1 to 3-12 are effective as nonlinear optical materials.

As previously mentioned, the Schiff base compounds according to the present invention are effective as high-performance nonlinear optical materials.

What is claimed is:

1. A Schiff base compound of formula (I)

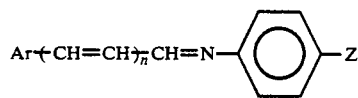

wherein Ar represents a phenyl group, which may have a substituent; n is 0 or 1; and Z represents

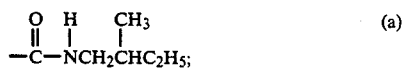

or

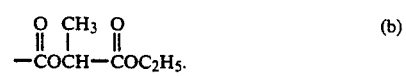

2. The Schiff base compound as claimed in claim 1, wherein said substituent of the phenyl group represented by Ar is selected from the group consisting of:
an amino group having as a substituent at least one alkyl group having 1 to 4 carbon atoms, a phenyl group or a benzyl group;
a hydroxyl group;
an alkoxyl group having 1 to 16 carbon atoms, which may have a phenyl group as a substituent;
a phenyl group which may have as a substituent an alkyl group having 1 to 6 carbon atoms or an alkoxyl group having 1 to 16 carbon atoms;
an alkyl group having 1 to 10 carbon atoms, which may have a phenyl group as a substituent;
a halogen;
an alkoxycarbonyl group with formula of —COO$C_lH_{2l+1}$ in which l is 1 to 16;
a cyano group; and
a nitro group.

* * * * *